United States Patent
Brodsky et al.

(10) Patent No.: US 7,645,621 B2
(45) Date of Patent: Jan. 12, 2010

(54) OPTICAL INSPECTION METHODS

(75) Inventors: Colin Brodsky, Salt Point, NY (US); Mary Jane Brodsky, Salt Point, NY (US); Sean Burns, Hopewell Junction, NY (US); Habib Hichri, Poughkeepsie, NY (US)

(73) Assignee: International Business Machines Corporation, Armonk, NY (US)

(*) Notice: Subject to any disclaimer, the term of this patent is extended or adjusted under 35 U.S.C. 154(b) by 252 days.

(21) Appl. No.: 11/872,900

(22) Filed: Oct. 16, 2007

(65) Prior Publication Data

US 2009/0097017 A1     Apr. 16, 2009

(51) Int. Cl.
*H01L 21/66* (2006.01)
*G01R 31/26* (2006.01)
*G01N 21/00* (2006.01)
*G01C 5/00* (2006.01)

(52) U.S. Cl. .................. 438/16; 356/237.4; 356/237.5; 430/30; 257/E21.53

(58) Field of Classification Search ................ 438/16; 356/237.4, 237.5; 430/30; 257/E21.53
See application file for complete search history.

(56) References Cited

U.S. PATENT DOCUMENTS

| | | | |
|---|---|---|---|
| 6,774,990 B2 | 8/2004 | Liang et al. | |
| 6,902,855 B2 | 6/2005 | Peterson et al. | |
| 7,042,564 B2 | 5/2006 | Shoham et al. | |
| 7,126,681 B1 | 10/2006 | Chen et al. | |
| 7,498,106 B2* | 3/2009 | Mui et al. | 430/30 |
| 2004/0063008 A1* | 4/2004 | Tabery et al. | 430/30 |
| 2006/0102839 A1 | 5/2006 | Bhaskar et al. | |
| 2006/0244958 A1* | 11/2006 | Furman et al. | 356/237.4 |
| 2007/0035728 A1 | 2/2007 | Kekare et al. | |

* cited by examiner

*Primary Examiner*—David A Zarneke
(74) *Attorney, Agent, or Firm*—Schmeiser, Olsen & Watts; Steven Capella

(57) ABSTRACT

Inspection methods. A method includes adhering an optical blocking layer directly onto and in direct mechanical contact with a semiconductor process wafer, the blocking layer being substantially opaque to a range of wavelengths of light; applying at least one layer over the blocking layer; and inspecting optically at least one wavelength at least one inspection area, the blocking layer extending substantially throughout the inspection area. An inspection method including adhering an optical absorbing layer to a semiconductor process wafer, where the absorbing layer is configured to substantially absorb a range of wavelengths of light; applying at least one layer over the absorbing layer; and inspecting optically at least one wavelength at least one inspection area of the process wafer. A manufacturing method including ascertaining if a defect is present within a photoresist layer, and changing a semiconductor manufacturing process to prevent the defect, if the defect is present.

1 Claim, 3 Drawing Sheets

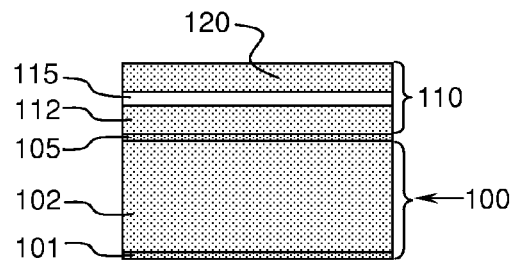
FIG. 1A
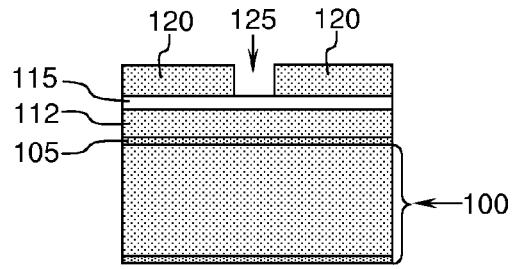
FIG. 1B
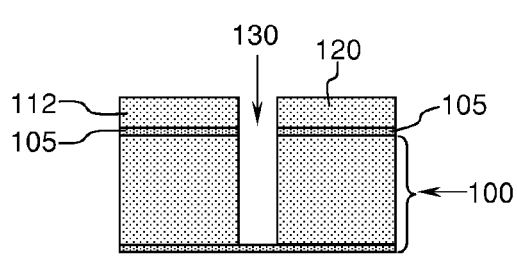
FIG. 1C
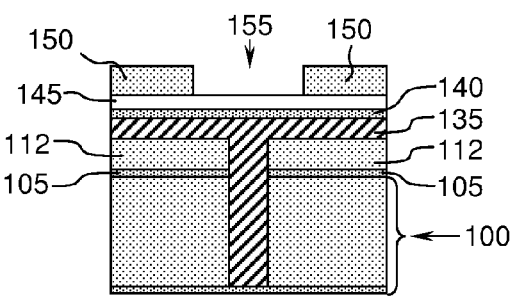
FIG. 1D
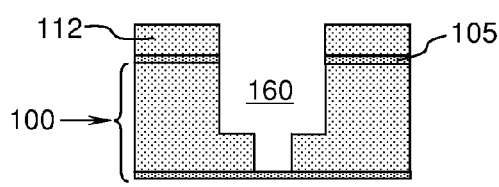
FIG. 1E
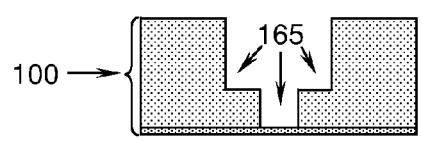
FIG. 1F
FIG. 1

OPTICAL INSPECTION METHODS

FIELD OF THE INVENTION

The invention generally relates to methods for optical inspection of substrates.

BACKGROUND OF THE INVENTION

The ability of optical inspection tools to provide high-value results may be a strong function of their ability to filter the inspection layer of interest from underlying prior level patterns that are not of interest. In post-lithography inspections, using techniques such as process window qualifications (PWQ), wafers may be inspected at the lithography step with multiple process conditions. Test macros for routine inspections may be generally performed on flat bare silicon monitors to simulate a production process. There are difficulties in routine inspections with product wafers that contain multiple film stacks, primarily due to interference from underlying films, and underlying film topography. This is particularly an issue in the back end of line (BEOL), where lithography focus budgets erode relative to intra-die topography. There exists a need for a method for inspecting real product substrates with topography that may influence scanner focus control in very non-obvious manners, in order to accurately assess the process center.

SUMMARY OF THE INVENTION

The present invention relates to an inspection method, said method comprising:

adhering an optical blocking layer directly onto and in direct mechanical contact with a semiconductor process wafer, said optical blocking layer being substantially opaque to a range of wavelengths of light;

applying at least one layer over said optical blocking layer, wherein a first layer of said at least one layer is adhered directly onto said optical blocking layer; and inspecting optically at least one wavelength within said range of wavelengths at least one inspection area of said at least one layer, said optical blocking layer extending substantially throughout said inspection area.

The present invention relates to a process wafer optical inspection method, said method comprising:

adhering an optical absorbing layer to a semiconductor process wafer, said optical absorbing layer configured to substantially absorb a range of wavelengths of light;

applying at least one layer over said optical absorbing layer, wherein a first layer of said at least one layer is adhered directly onto said optical absorbing layer; and inspecting optically at least one wavelength within said range of wavelengths at least one inspection area of said process wafer having said optical absorbing layer, said optical absorbing layer extending substantially throughout said inspection area.

The present invention relates to a manufacturing method, comprising:

providing an integrated semiconductor wafer having an optical blocking layer, said blocking layer configured to block a range of wavelengths of light;

adhering a photoresist layer to said wafer having said blocking layer, wherein said adhering has resulted from a semiconductor manufacturing process.

inspecting optically at least one wavelength within said range of wavelengths at least one inspection area of said photoresist layer, said optical blocking layer extending substantially throughout said inspection area;

based on said inspecting, ascertaining if a defect is present within said photoresist layer; and changing said semiconductor manufacturing process to prevent said defect, if said defect is present within said photoresist layer.

BRIEF DESCRIPTION OF THE DRAWINGS

The features of the invention are set forth in the appended claims. The invention itself, however, will be best understood by reference to the following detailed description of illustrative embodiments when read in conjunction with the accompanying drawings.

FIG. 1A is an illustration of a cross-section of a substrate having an optical blocking layer, in accordance with embodiments of the present invention.

FIG. 1B is an illustration of the substrate and layers of FIG. 1A after patternwise imaging and developing a radiation sensitive resist layer, in accordance with embodiments of the present invention.

FIG. 1C is an illustration of the substrate and layers of FIG. 1B after the radiation sensitive resist layer and ARC layer have been stripped away, and a via has been etched into the substrate, in accordance with embodiments of the present invention.

FIG. 1D is an illustration of the substrate and layers of FIG. 1C after additional layer deposition and processing, in accordance with embodiments of the present invention.

FIG. 1E is an illustration of the substrate in FIG. 1D, after etching a trench and stripping away the radiation sensitive resist layer, the antireflective coating, the low temperature oxide coating, and the organic interlayer planarizing layer, in accordance with embodiments of the present invention.

FIG. 1F is an illustration of the substrate in FIG. 1E after removal of the optical blocking layer and hard mask layer, in accordance with embodiments of the present invention.

DETAILED DESCRIPTION OF THE INVENTION

Figure 2:
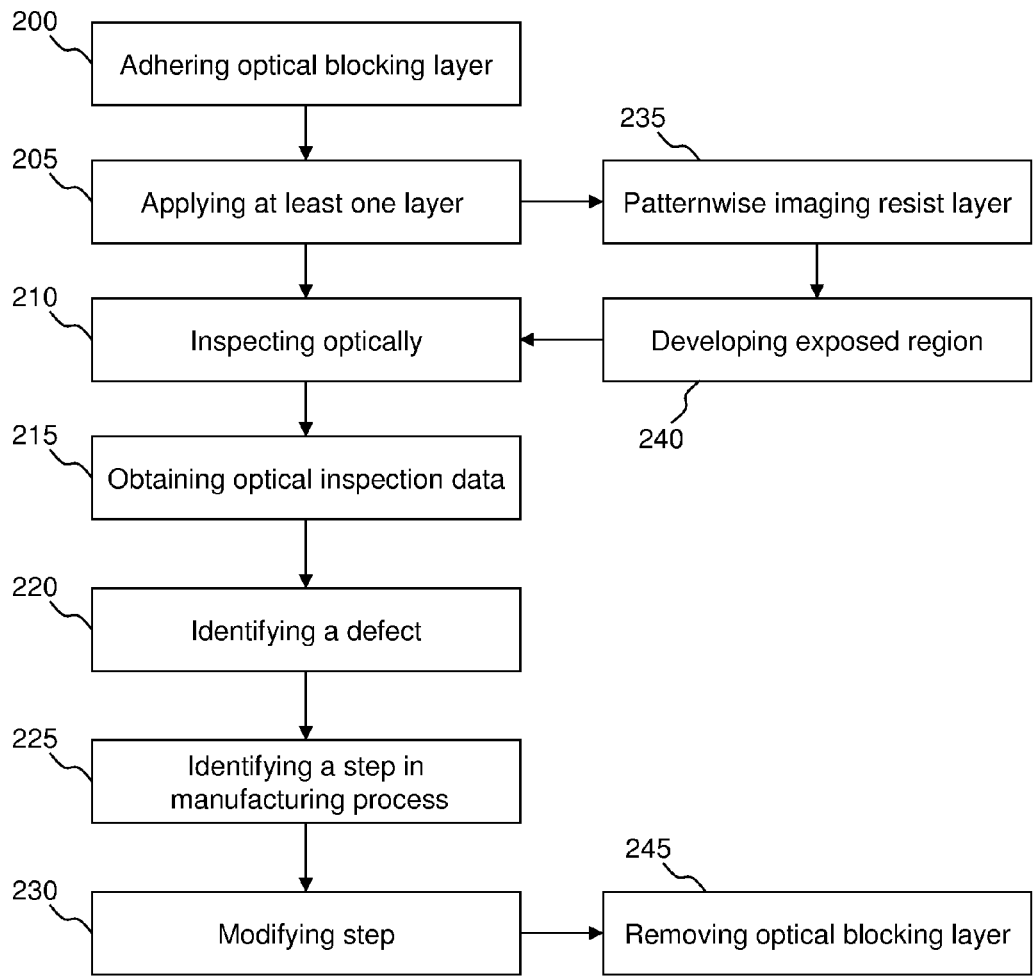
FIG. 2 is a flow chart of steps in an inspection method utilizing an optical blocking layer, in accordance with embodiments of the present invention.

Although certain embodiments of the present invention will be shown and described in detail, it should be understood that various changes and modifications may be made without departing from the scope of the appended claims. The scope of the present invention will in no way be limited to the number of constituting components, the materials thereof, the shapes thereof, the relative arrangement thereof, etc., and are disclosed simply as examples of embodiments. The features and advantages of the present invention are illustrated in detail in the accompanying drawings, wherein like reference numerals refer to like elements throughout the drawings. Although the drawings are intended to illustrate the present invention, the drawings are not necessarily drawn to scale.

The present invention relates to optical blocking and absorbing layers which may be inserted into a manufacturing process flow for a semiconductor wafer to enable optical inspection, such as brightfield inspection, where the optical blocking and absorbing layers may be tuned for an inspection wavelength of interest. An optical blocking layer may be substantially opaque to a range of wavelengths of light, which may include the inspection wavelength of interest. An optical absorbing layer may be configured to substantially absorb a range of wavelengths of light, which may include the inspection wavelength of interest.

The optical blocking and absorbing layers may be adhered to a substrate in such a fashion that the optical blocking and absorbing layers may be disposed beneath film stacks that may be etched or modified, thus enabling defect source partitioning between processing steps such as post hardmask deposition, post Via lithography, post Via reactive ion etching (RIE), post interlayer planarizing film coating/cure, post low temperature oxide (LTO) deposition, and post trench lithography and RIE. Such optical blocking and absorbing layers may be configured to reflect and/or absorb optical inspection wavelengths that may otherwise penetrate a film stack of material deposited in a semiconductor manufacturing process, thus preventing the collection of inspection information from underlying layers that may not be of interest. Without the use of such optical blocking and absorbing layers, the inspection signal from these underlying layers may increase and the signal-to-noise ratio to detect the layer of interest may decrease, where the ratio may reach a level which may render the inspection worthless.

FIG. 1A is an illustration of a cross-section of a substrate 100 having an optical blocking layer 105 adhered directly onto and in direct mechanical contact with the substrate 100. The substrate 100 may include a semiconducting material, an insulating material, a conductive material or any combination thereof, including multilayered structures. Thus, for example, substrate 100 may be a semiconducting material such as Si, SiGe, SiGeC, SiC, GaAs, InAs, InP and other III/V or II/VI compound semiconductors. The substrate 100 may be, for example, a process wafer such as that produced in various steps of a semiconductor manufacturing process, such as an integrated semiconductor wafer. The substrate 100 may comprise more than one layer, such as layer 101 and layer 102 in FIG. 1A. The substrate 100 may be a layered substrate such as, for example, Si/SiGe, Si/SiC, silicon-on-insulators (SOIs) or silicon germanium-on-insulators (SGOIs). The substrate may comprise layers such as a dielectric layer, a barrier layer for copper such as SiC, a metal layer such as copper, a silicon layer, a silicon oxide layer, the like, or combinations thereof. The substrate 100 may comprise an insulating material such as an organic insulator, an inorganic insulator or a combination thereof including multilayers. The substrate 100 may comprise a conductive material, for example, polycrystalline silicon (polySi), an elemental metal, alloys of elemental metals, a metal silicide, a metal nitride, or combinations thereof, including multilayers.

In some embodiments, the substrate 100 may include a combination of a semiconducting material and an insulating material, a combination of a semiconducting material and a conductive material or a combination of a semiconducting material, an insulating material and a conductive material. An example of a substrate that includes a combination of the above is an interconnect structure.

The optical blocking layer 105 may be substantially optically opaque to a range of wavelengths of light, and may comprise materials such as tantalum nitride, tungsten nitride, gallium nitride, titanium nitride, tantalum, titanium, hafnium oxide, or combinations thereof. The optical blocking layer may be applied to the substrate through processes such as sputtering, chemical vapor deposition (CVD); plasma enhanced chemical vapor deposition (PECVD), spin-coating, etc.

The optical blocking layer may be configured such that the maximum possible fraction of light may be reflected off the optical blocking layer, and that light which does enter the optical blocking layer is quickly attenuated. Thus, light passing through only inspection layers of interest may reflect back to the detector of an inspection device, restricting the optical inspection data to the layers of interest, where the optical inspection data may be used in die-to-die or within-die array comparisons between a test sample and an accepted standard specimen having no defects.

The film may be sufficiently thin such that it exhibits a highly conformal mapping of the existing substrate topography and may preserve substrate topography while blocking signals from lower layers embedded within the substrate topography. For example, the optical blocking layer may have a thickness in a range from about 25 angstroms to about 500 angstroms, such as from about 25 angstroms to about 100 angstroms.

At least one layer 110 may be applied over the optical blocking layer 105, where a first layer 112 of the at least one layer 110 may be applied directly onto the optical blocking layer 105, and subsequent layers may be applied on top of the first layer 110 in succession.

The at least one layer 110 may comprise a hard mask layer, an antireflective coating such as BARC, a radiation sensitive resist layer such as a photoresist layer, an oxide layer, a metal layer, a metal oxide layer, a nitride layer, a dielectric layer, the like, or combinations thereof. For example, in FIG. 1, the at least one layer 110 may comprise a hard mask layer 112, an ARC layer 115, and a radiation sensitive resist layer 120.

The hard mask layer 112 may comprise a dielectric layer such as a carbon-doped oxide dielectric comprised of Si, C, O, and H (SiCOH), a low dielectric etch stop/barrier layer containing Si, C, and H such as BLOK and Nitrogen rich BLOK (NBLOK), tetraethylorthosilicate (TEOS), a nitride layer such as a high density plasma (HDP) nitride layer, or combinations thereof.

At least one inspection area of the at least one layer, such as a hard mask layer 112, may be inspected optically at least one wavelength within the range of wavelengths to which the optical blocking layer 105 is optically opaque. The inspection area may have topographical variation, such as trenches and vias for example, which may be present from previous processing of the substrate or may be created in subsequent processing after which optical inspection may be performed. The optical blocking layer may extend substantially throughout the inspection area. The optical blocking layer may reflect optical inspection wavelengths, block or prevent inspection wavelength penetration to lower layers of the substrate 100, and prevent collection of information from underlying layers which may not be of interest. The optical inspection may be performed as each subsequent layer is adhered to the layer stack or when layers are modified by the manufacturing process (such as etching, exposure, or developing), thus allowing for the inspection of each layer as it is applied and processed, and for the identification of any defects which may be present in the applied layers.

FIG. 1B is an illustration of the substrate 100 and layers of FIG. 1A after patternwise imaging and developing a radiation sensitive resist layer 120. The radiation sensitive resist 120 layer may be patternwise imaged through a mask, exposing at least one region of the radiation sensitive resist layer 120 to radiation, resulting in production of an acid catalyst in the exposed at least one region of the radiation sensitive resist layer 120. The exposed region may be developed, resulting in the removal of regions 125 of the radiation sensitive resist layer 120, wherein a relief pattern from the radiation sensitive resist layer 120 may remain following the removal. The radiation sensitive resist layer 120 having the relief pattern may be optically inspected as described above, wherein the optical blocking layer 105 may reflect and/or attenuate the wavelength of light used in the optical inspection.

FIG. 1C is an illustration of the substrate 100 and layers of FIG. 1B after the radiation sensitive resist layer 120 and ARC layer 115 have been stripped away, and a via 130 has been etched into the substrate 100, such as with an etching process, such as a plasma for example. The optical blocking layer 105 may be utilized to optically inspect the hard mask layer 112 and the via 130 as described above, where such an inspection may identify a defect in the hard mask layer 112 or the configuration of the via 130, which may have been caused by an etching step in a semiconductor manufacturing process, for example.

FIG. 1D is an illustration of the substrate 100 and layers of FIG. 1C after additional layer deposition and processing where additional layers have been adhered over the optical blocking layer 105. As illustrated in FIG. 1D, additional layers may be adhered over the substrate 100 having an optical blocking layer 105, such as an organic interlayer planarizing layer 135, a low temperature oxide layer 140, an antireflective coating 145, and a radiation sensitive resist layer 150, for example. As each additional layer is adhered to the substrate 100, the layers may be optically inspected for defects using the optical blocking layer 105 to reflect and/or attenuate the optical inspection wavelengths, thus preventing penetration to lower layers of the substrate 100 and collecting information from underlying layers that are not of interest. For example, the organic interlayer planarizing layer 135 may be inspected optically after is adhered to the hard mask layer 112, where optical inspection data may be obtained for the organic interlayer planarizing layer 135, without obtaining data from the substrate 100 and layers therein. Examples of suitable materials for the organic planarizing layer include JSR NFC series, HM series, or Shin Etsu ODL series. Specific examples include JSR NFC-1400, HM8005, Shin Etsu ODL-30, ODL-50, and ODL-63.

As illustrated in FIG. 1D, the radiation sensitive resist layer 150 may be patternwise exposed and developed as described above, where portions 155 of the radiation sensitive resist layer 150 may be removed during developing to leave a relief pattern in the radiation sensitive resist layer 150. The radiation sensitive resist layer 150 may be inspected optically for defects as described above.

FIG. 1E is an illustration of the substrate in FIG. 1D, after etching a trench 160 and stripping away the radiation sensitive resist layer 150, the antireflective coating 145, the low temperature oxide coating 140, and the organic interlayer planarizing layer 135. The presence of the optical blocking layer 105 may allow for optical inspection of the pattern of the trench 160. The optical blocking layer 105 may be removed by a process such as chemical mechanical polishing (CMP), etching, etc. FIG. 1F is an illustration of the substrate 100 in FIG. 1E after removal of the optical blocking layer 105 and hard mask layer 112, to leave a substrate 100 having the formation 165 created from the via 130 of FIG. 1C and the trench 160 of FIG. 1E.

The optical blocking layer 105 described above for the examples illustrated in FIGS. 1L-1F may alternatively be an optical absorbing layer, wherein the optical absorbing layer may be configured to substantially absorb a range of wavelengths of light used in an optical inspection technique. For example, as with the optical blocking layer described above, an optical absorbing layer may be adhered directly to a substrate (such as a semiconductor process wafer), and at least one layer may be applied over the optical absorbing layer, where a first layer of the at least one layer may be adhered directly onto the optical absorbing layer. At least one inspection area of the substrate may be inspected optically at least one wavelength within the range of absorbed wavelengths, where the optical absorbing layer may extend substantially throughout the inspection area.

The optical absorbing layer may be configured to substantially absorb light at inspection wavelengths and thus prevent inspection data from being retrieved from light reflecting of layers below the optical absorbing layer which may not be of interest. For example, the optical absorbing layer may be configured to absorb greater than about 95% of light of at least one wavelength, such as the inspection wavelength, within a range of absorbing wavelengths. In one embodiment the optical absorbing layer may have an imaginary index of refraction (k) between about 0.1 and about 0.8 for light having a wavelength in a range from about 193 nanometers (nm) to about 260 nm. For example, the optical absorbing layer may have an imaginary index of refraction of 0.8 for light having a wavelength of about 193 nm, where an optical inspection light may utilize single-wavelength light at about 193 nm, such as may be generated by laser-based optical inspection system. In another embodiment, the optical absorbing layer may have an imaginary index of refraction (k) greater than about 0.2 for light having a wavelength in a range from about 260 nanometers to about 360 nanometers. In another embodiment, the optical absorbing layer may have an imaginary index of refraction less than about 0.1 for light having a wavelength greater than 450 nanometers. In one embodiment the optical absorbing layer may have a thickness from about 10 nanometers to 2000 nanometers, such as from about 80 nanometers to about 500 nanometers.

The optical absorbing layer may comprise an organic compound. In one embodiment the organic compound may have a composition having at least 70% carbon by weight. In another embodiment, the organic compound may have a molecular weight in a range from about 2,000 to about 25,000 grams/mole. The organic compound may be a polymer. The organic compound may comprise, for example, a porphyrin, a phthalocyanine, tartrazine, phenolic polymer, polyhydroxystyrene-based polymer, derivatives thereof, or combinations thereof. It will be recognized that there exist numerous organic compounds having sufficient absorption characteristics at inspection wavelengths and that the examples here are merely illustrative of all such compounds which are included within embodiments of the present invention.

FIG. 2 is a flow chart of steps in an inspection method utilizing an optical blocking layer. In step 200, an optical blocking layer may be adhered to a substrate, such as a process wafer used in semiconductor manufacturing, for example. The optical blocking layer may be as described above and may be adhered directly onto and in direct mechanical contact with the substrate. The optical blocking layer may be substantially opaque to a range of wavelengths of light.

In step 205, at least one layer is applied over the optical blocking layer adhered to the substrate in step 200, where a first layer of the at least one layer may be adhered directly onto the optical blocking layer. The at least one layer may comprise a hard mask layer, an antireflective coating (ARC) such as BARC (bottom antireflective coating), a radiation sensitive resist layer such as a photoresist, an oxide layer, a metal layer, a metal oxide layer, a nitride layer, a dielectric layer, the like, or combinations thereof. For example, the first layer of the at least one layer may comprise a hard mask layer, where an antireflective coating may be adhered directly onto the hard mask layer, and a radiation sensitive resist layer may be adhered directly onto the antireflective coating layer, such as the example illustrated in FIG. 1A.

In step 210, at least one inspection area of the at least one layer may be inspected optically at least one wavelength within the range of wavelengths in which the optical blocking layer is substantially opaque. The optical blocking layer may extend substantially throughout the inspection area.

In step 235, the radiation sensitive resist layer may be patternwise imaged, where a radiation or particle beam source may project radiation or energetic particles through a patterned mask onto the radiation sensitive resist layer. The mask may have a pattern of masked sections which may be substantially opaque to the radiation or impenetrable to the energetic particles, and unmasked sections which may be substantially transparent to the radiation or penetrable to the energetic particles. Radiation (such as ultra violet, deep ultra violet, extreme ultraviolet, x-rays, etc.) or particles (such as electron beam, ion beam, etc.) passing through the unmasked sections may be transmitted to the film to be absorbed in the exposed regions of the radiation sensitive resist layer. In one embodiment, the radiation or particles may induce the production of an acid catalyst in the exposed regions of the radiation sensitive resist layer, where unexposed regions may not produce an acid catalyst, and wherein exposure to the radiation or energetic particles may render the exposed regions soluble in a developer. In another embodiment, the radiation or particles may induce the production of a base catalyst in the exposed regions of the radiation sensitive resist layer, and wherein exposure to the radiation or energetic particles may render the exposed regions soluble in a developer.

In step 240, the radiation sensitive resist layer may be developed in an appropriate developer, where soluble regions of the radiation sensitive resist layer may be removed, leaving a relief pattern from the radiation sensitive resist layer remaining, such as the example illustrated in FIG. 1B. The developer may be an organic or aqueous based developer, such as an alkaline aqueous developer, such as tetramethylammonium hydroxide, for example. After developing in step 240, the process may return to step 210 where the relief pattern may be inspected optically as described above.

The example of pattern-wise imaging the radiation sensitive resist layer in step 235 and step 240 is not meant to limit the scope of the present invention with regarding to producing a relief pattern which may be inspected as described herein. For example, the relief pattern may be produced by such processes as imprint lithography to produce a relief pattern on the surface of a layer substrate.

In step 215, optical inspection data may be obtained from the optical inspection of step 210. Inspection data may comprise scanned image information of the inspection area in comparison to image information for a known standard of the same pattern, such as that of a defect free sample or adjacent reference die. Such an inspection may be performed for each step of a process depositing, removing, or modifying layers on the substrate.

In step 220 a defect may be identified in at least one layer based on the optical inspection data obtained in step 215. Based on inspecting the at least one layer, a user may ascertain whether a defect is present in the inspected layer (such as in a radiation sensitive layer, for example) by comparison with a known standard. Such defects may include random or systematic defects such as bridging between surface features, missing features, etc.

In step 225, a step of a manufacturing process may be identified as having caused the defect identified in step 220. For example, the substrate may be a process wafer and the at least one layer may be applied to the blocking layer in a semiconductor manufacturing process. For example, the defect in the sample may be caused by damage or a defect in the mask used during exposure of the radiation sensitive resist layer. In another example, the defect may be caused by incorrect process conditions in the steps taken for adhering or etching the at least one layer over the optical blocking layer.

In step 230, in response to identifying the manufacturing step in step 225 which caused the defect, the manufacturing step may be modified to prevent the defect from recurring in the process. For example, a damaged or defective mask may be repaired or replaced, or process conditions may be adjusted and new process tolerances may be implemented to reduce the chance of defect recurrence.

In step 245, the optical blocking layer may be removed, such as by chemical mechanical polishing, reactive ion removal or wet chemical stripping, for example.

Figure 3:
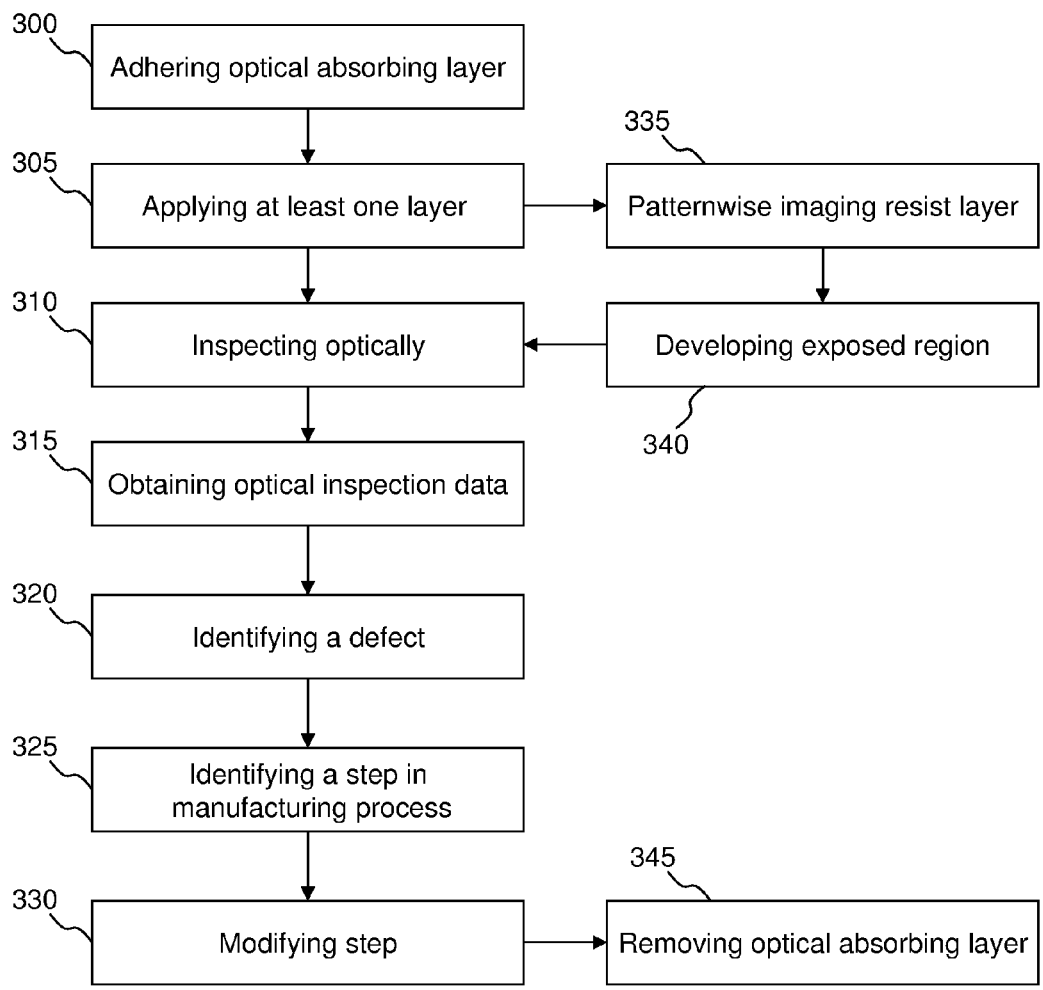
FIG. 3 is a flow chart of steps in an inspection method utilizing an optical absorbing layer, in accordance with embodiments of the present invention.

FIG. 3 is a flow chart of steps in an inspection method utilizing an optical absorbing layer. In step 300, an optical absorbing layer may be adhered to a substrate, such as a process wafer used in semiconductor manufacturing, for example. The optical absorbing layer may be as described above and may be adhered directly onto and in direct mechanical contact with the substrate. The optical absorbing layer may be configured to substantially absorb a range of wavelengths of light.

In step 305, at least one layer is applied over the optical absorbing layer adhered to the substrate in step 300, where a first layer of the at least one layer may be adhered directly onto the optical absorbing layer. The at least one layer may comprise a hard mask layer, an antireflective coating (ARC) such as BARC, a radiation sensitive resist layer such as a photoresist, an oxide layer, a metal layer, a metal oxide layer, a nitride layer, a dielectric layer, the like, or combinations thereof. For example, the first layer of the at least one layer may comprise a hard mask layer, where an antireflective coating may be adhered directly onto the hard mask layer, and a radiation sensitive resist layer may be adhered directly onto the antireflective coating layer.

In step 310, at least one inspection area of the at least one layer may be inspected optically at least one wavelength within the range of wavelengths in which the optical absorbing layer is configured to substantially absorb. The optical absorbing layer may extend substantially throughout the inspection area.

In step 335, the radiation sensitive resist layer may be patternwise imaged, where a radiation or particle beam source may project radiation or energetic particles through a patterned mask onto the radiation sensitive resist layer. The mask may have a pattern of masked sections which may be substantially opaque to the radiation or impenetrable to the energetic particles, and unmasked sections which may be substantially transparent to the radiation or penetrable to the energetic particles. Radiation (such as ultra violet, deep ultra violet, extreme ultraviolet, x-rays, etc.) or particles (such as electron beam, ion beam, etc.) passing through the unmasked sections may be transmitted to the film to be absorbed in the exposed regions of the radiation sensitive resist layer. In one embodiment, the radiation or particles may induce the production of an acid catalyst in the exposed regions of the radiation sensitive resist layer, where unexposed regions may not produce an acid catalyst, and wherein exposure to the radiation or energetic particles may render the exposed regions soluble in a developer. In another embodiment, the radiation or particles may induce the production of a base catalyst in the exposed regions of the radiation sensitive resist layer, and wherein exposure to the radiation or energetic particles may render the exposed regions soluble in a developer.

In step 340, the radiation sensitive resist layer may be developed in an appropriate developer, where soluble regions of the radiation sensitive resist layer may be removed, leaving a relief pattern from the radiation sensitive resist layer remaining. The developer may be an organic or aqueous based developer, such as an alkaline aqueous developer, such as tetramethylammonium hydroxide, for example. After developing in step 340, the process may return to step 310 where the relief pattern may be inspected optically as described above.

In step 315, optical inspection data may be obtained from the optical inspection of step 310. Inspection data may comprise scanned image information of the inspection area in comparison to image information for a known standard of the same pattern, such as that of a defect free sample. Such an inspection may be performed for each step of a process depositing, removing, or modifying layers on the substrate.

In step 320 a defect may be identified in at least one layer based on the optical inspection data obtained in step 315. Based on inspecting the at least one layer, a user may ascertain whether a defect is present in the inspected layer (such as in a radiation sensitive layer, for example) by comparison with a known standard. Such defects may include random or systematic defects such as bridging between surface features, missing features, etc.

In step 325, a step of a manufacturing process may be identified as having caused the defect identified in step 320. For example, the substrate may be a process wafer and the at least one layer may be applied to the blocking layer in a semiconductor manufacturing process. For example, the defect in the sample may be caused by damage or a defect in the mask used during exposure of the radiation sensitive resist layer. In another example, the defect may be caused by incorrect process conditions in the steps taken for adhering or etching the at least one layer over the optical absorbing layer.

In step 330, in response to identifying the manufacturing step in step 325 which caused the defect, the manufacturing step may be modified to prevent the defect from recurring in the process. For example, a damaged or defective mask may be repaired or replaced, or process conditions may be adjusted and new process tolerances may be implemented to reduce the chance of defect recurrence.

In step 345, the optical blocking layer may be removed, such as by chemical mechanical polishing, for example.

The foregoing description of the embodiments of this invention has been presented for purposes of illustration and description. It is not intended to be exhaustive or to limit the invention to the precise form disclosed, and obviously, many modifications and variations are possible. Such modifications and variations that may be apparent to a person skilled in the art are intended to be included within the scope of this invention as defined by the accompanying claims.

What is claimed:

1. An inspection method, said method comprising:
adhering an optical blocking layer directly onto and in direct mechanical contact with a semiconductor process wafer using chemical vapor deposition, said optical blocking layer being substantially opaque to a range of wavelengths of light, said optical blocking layer comprising hafnium oxide and having a thickness in a range from about 25 angstroms to about 100 angstroms;
applying at least one layer over said optical blocking layer in a semiconductor manufacturing process, wherein a first layer of said at least one layer is adhered directly onto said optical blocking layer, said first layer comprising a hard mask layer comprising a carbon-doped oxide dielectric comprising Si, C, O, and H, said applying said at least one layer over said optical blocking layer comprising adhering an antireflective coating directly onto said hard mask layer and adhering a radiation sensitive resist layer directly onto said antireflective coating layer;
patternwise imaging said radiation sensitive resist layer through a mask, exposing at least one region of said radiation sensitive resist layer to radiation, resulting in production of an acid catalyst in said exposed at least one region of said radiation sensitive resist layer;
developing said exposed at least one region, resulting in removal of regions of said radiation sensitive resist layer, wherein a relief pattern from said radiation sensitive resist layer remains following said removal;
after said developing, inspecting optically at least one wavelength within said range of wavelengths at least one inspection area of said at least one layer, said at least one inspection area having a topographical variation, said optical blocking layer extending substantially throughout said inspection area;
obtaining optical inspection data from said inspecting, said optical inspection data comprising scanned image information of said at least one inspection area;
identifying based on said optical inspection data a defect in said at least one layer;
identifying a step in said semiconductor manufacturing process having caused said defect;
responsive to said identifying said step, modifying said step in said semiconductor manufacturing process to prevent said defect; and
removing said optical blocking layer using a chemical mechanical polishing process.

* * * * *